United States Patent [19]

Chikama

[11] 4,279,246
[45] Jul. 21, 1981

[54] DEVICE FOR PREVENTING CLOUDING OF AN OBSERVING WINDOW

[75] Inventor: Toshio Chikama, Tokyo, Japan

[73] Assignee: Machida Endoscope Co., Ltd., Tokyo, Japan

[21] Appl. No.: 44,596

[22] Filed: Jun. 1, 1979

[30] Foreign Application Priority Data

Jun. 19, 1978 [JP] Japan .............................. 53-082938[U]

[51] Int. Cl.³ ................................................ A61B 1/06
[52] U.S. Cl. .......................................... 128/6; 350/61
[58] Field of Search .......................................... 128/3–9, 128/303.1; 350/96.26, 61, 66; 356/241; 219/219

[56] References Cited

U.S. PATENT DOCUMENTS 4,076,018  2/1978  Heckele .................................. 128/6

FOREIGN PATENT DOCUMENTS 1082146  5/1960  Fed. Rep. of Germany ............. 350/61

Primary Examiner—Kyle L. Howell
Assistant Examiner—Arthur S. Rose
Attorney, Agent, or Firm—Peter L. Berger

[57] ABSTRACT

The present invention discloses a device for preventing clouding of an observing window, utilizing heat rays of a light source. A converter is provided near the observing window for changing light into heat and the light is guided to said converter from light transmitting optic bundles. Then, a part of the light is changed into heat by this converter and the observing window is warmed by the heat in order to prevent the clouding.

8 Claims, 4 Drawing Figures

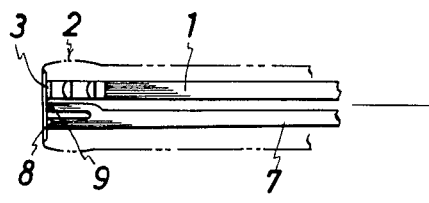
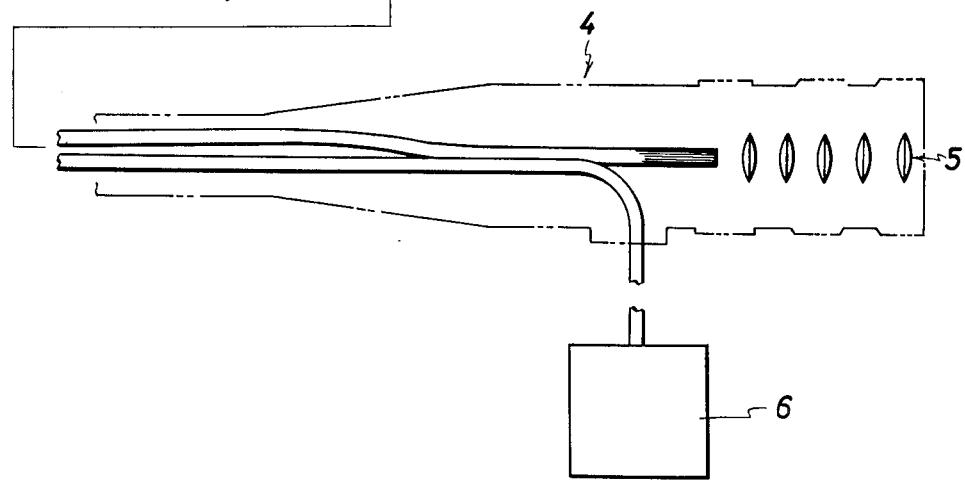
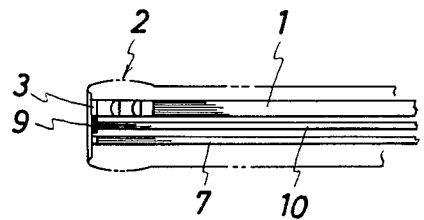
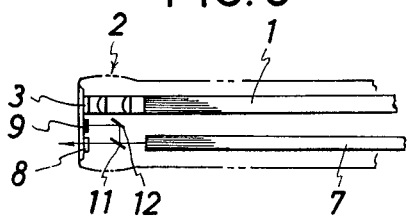
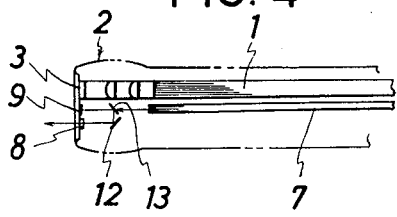

DEVICE FOR PREVENTING CLOUDING OF AN OBSERVING WINDOW

BACKGROUND OF THE INVENTION

A. Field of the Invention

The present invention mainly relates to a medical or industrial endoscope, or more particularly, to a device for preventing clouding of an observing window.

B. Description of the Prior Art

An endoscope is an optical instrument for observing and treating the body cavity, such as the stomach or intestines, by inserting a distal examining end of it to said body cavity. Flexible optic bundles are used for illuminating the object from said distal examining end and image-transmitting optic bundles are provided for optically coupling the observing window and an eyepiece of a grip end.

By the way, it often occurs that the observing window is covered by dew when the endoscope is inserted in the body cavity. This is because temperature of the observing window is lower than that of the body cavity at the beginning.

In the prior art, as detailed in the U.S. Pat. No. 4,076,018 to Heckele, a device is proposed for electrically warming the observing window. But, such a device is complicated and, moreover, it is undesirable to apply electric means to an instrument which is used in the body cavity.

SUMMARY OF THE INVENTION

An illuminant such as Xenon lamp is used for the light source for generating an illumination. Said Xenon lamp generates infrared rays, namely the heat rays, in addition to the visible rays and these rays can be guided by optic bundles at will. Therefore, the heat rays can be utilized to warm the observing window.

Accordingly, it is the first object of the invention to obtain a device for preventing clouding of an observing window by warming it with said heat rays.

It is the second object of the invention to provide a simple device for preventing clouding of an observing window which uses light-transmitting optic bundles.

To achieve these objects, means are provided near the observing window for changing light into heat and the light is guided to the means from the light-transmitting optic bundles. A part of the light is then changed into heat by the means and the observing window is warmed by the heat to prevent clouding.

The above- and further objects and novel features of the invention will more fully appear from the following detailed description when the same is read in connection with the accompanying drawings. It is to be expressly understood, however, that the drawings are for purpose of illustration only and are not intended as a definition of the invention.

BRIEF DESCRIPTION OF THE DRAWINGS

FIG. 1 is a schematic cross-sectional view of a device for preventing clouding of an observing window according to an embodiment of the present invention.

FIG. 2 is a partial cross-sectional view of a device for preventing clouding of an observing window according to another embodiment of the present invention.

FIG. 3 is a partial cross-sectional view of a device for preventing clouding of an observing window according to further embodiment of the present invention in which a heat ray reflector is provided.

FIG. 4 is a partial cross-sectional view of a device for preventing clouding of an observing window according to another embodiment of the present invention in which a heat ray permeable mirror is provided.

DETAILED DESCRIPTION OF PREFERRED EMBODIMENTS

In FIG. 1, numeral 1 indicates flexible image-transmitting optic bundles which optically communicate an observing window 3 and a distal examining end 2 and an eyepiece 5 of a grip end 4. Numeral 6 indicates a light source which, for example, is composed of a Xenon lamp. Said Xenon lamp generates infrared rays, namely heat rays, in addition to visible rays. Numeral 7 indicates light-transmitting optic bundles by way of which the light from the light source 6 is guided to an illuminating window 8 at the distal examining end 2. A part of the light-transmitting optic bundles 7 is branched at the forward end and the branch is opposed to a metallic portion near the observing window 3. The metallic portion such as means for holding an objective lens is situated near the observing window 3. Therefore, the branch is opposed to the metallic portion in order to change the light into heat.

In addition, a metallic thermal plate 9 may especially be provided near the observing window 3. The thermal plate 9 is, for example, composed of a black body which absorbes the heat rays transmitted by the light-transmitting optic bundles 7 to change it into heat.

Besides, as shown in FIG. 2, optic bundles 10 for transmitting heat rays only may be provided in addition to the light-transmitting optic bundles 7.

Further, the thermal plate 9 may be attached to the observing window 3 or the observing window 3 may be surrounded by the thermal plate 9.

Moreover, a part of the forward end of the light-transmitting optic bundles 7 may be covered by the thermal plate 9.

Now, the operation of the above-said device will be described hereinunder.

A part of the light transmitted from the light source 6 by way of the light-transmitting optic bundles 7 is changed into heat by the thermal plate 9 when the endoscope is inserted into the body cavity. Thereby, the observing window 3 is warmed by the heat to equalize the temperature in the body cavity and that of the observing window 3. For this reason, clouding of the observing window 3 can be prevented.

The construction of the device can be simplified because the device is composed of the light source 6 and the light-transmitting optic bundles 7 which are necessarily provided in the endoscope.

Other embodiments will be described with reference to FIGS. 3 and 4.

In FIG. 3, a heat ray reflector 11 is provided between the forward end of the light-transmitting optic bundles 7 and the illuminating window 8. Numeral 12 indicates a reflector which is opposed to the heat ray reflector 11.

Among the rays transmitted by the light-transmitting optic bundles 7, the visible rays pass through the heat ray reflector 11 to the illuminating window 8. But, the heat rays are reflected by the heat ray reflector 11 and the reflector 12 to the metallic portion around the observing window 3 or the thermal plate 9. And then, the rays are changed into heat to warm the observing window 3. Accordingly, the observing window 3 can be prevented from clouding.

In FIG. 4, a heat ray permeable mirror 13 is provided between the forward end of the light-transmitting optic bundles 7 and the thermal plate 9. The reflector 12 is opposed to the heat ray permeable mirror 13. Among the rays transmitted by the light-transmitting optic bundles 7, the heat rays pass through the heat ray permeable mirror 13 to the thermal plate 9 and the visible rays are transferred to the illuminating window 8 via the reflector 12. The thermal plate 9 then changes the rays into heat to warm the observing window 3.

While there have been shown and described and pointed out the fundamental novel features of the invention as applied to preferred embodiments, it will be understood, however, that the various omissions and substitutions and changes in the form and details may be made by those skilled in the art without departing from the spirit of the invention.

What is claimed is:

1. In an endoscope having a forward examining end including an observing window, an image transmitting optic bundle positioned to transmit an image at said forward end, an illuminating window, a light-transmitting optic bundle, and a light source optically aligned with said light-transmitting optic bundle, a portion of the light emitted from said source being directed through said illuminating window into the field of view of said observing window by way of said light transmitting optical bundle, converter means for converting light into heat, another portion of the light emitted from said source being directed into said converter means by way of said light transmitting optical bundle, said converter means being attached to said forward examining end in the region of said observing window such that the heat generated acts to warm said observing window and prevent clouding.

2. Device for preventing clouding of an observing window of an endoscope according to claim 1, wherein said converter means comprises a metallic thermal plate.

3. Device for preventing clouding of an observing window of an endoscope according to claim 2, wherein the thermal plate is attached to the observing window.

4. Device for preventing clouding of an observing window of an endoscope according to claim 2, wherein a part of the forward end of the light-transmitting optic bundles is covered by the thermal plate.

5. Device for preventing clouding of an observing window of an endoscope according to claim 1, wherein said light transmitting optical bundle comprises two separate optic bundles, one of said bundles acting to transmit heat rays and the other of said bundles acting to transmit visible light rays.

6. Device for preventing clouding of an observing window according to claim 1, wherein a heat ray reflector is provided between the forward end of the light-transmitting optic bundles and said illuminating window and the visible rays are transferred to said illuminating window, while the heat rays are carried to the converter means.

7. Device for preventing clouding of an observing window according to claim 1, wherein a heat ray permeable mirror is provided between the forward end of the light-transmitting optic bundles and the converter means and only the heat rays are transferred to said converter means.

8. Device for preventing clouding of an observing window of an endoscope according to claim 1, wherein the forward end of the light-transmitting optic bundles has a branch and the branch is opposite to the said converter means.

* * * * *